United States Patent [19]

Mohiuddin et al.

[11] Patent Number: 4,889,534
[45] Date of Patent: Dec. 26, 1989

[54] OSTOMY APPLIANCE WITH THREE-LEMENT COUPLING RING ASSEMBLY

[75] Inventors: Mahmood Mohiuddin, Lake Zurich; Barry L. Schneider, Deerfield; Paul O. Kay, Libertyville, all of Ill.

[73] Assignee: Hollister Incorporated, Libertyville, Ill.

[21] Appl. No.: 236,279

[22] Filed: Aug. 23, 1988

Related U.S. Application Data

[63] Continuation of Ser. No. 937,825, Dec. 4, 1986, abandoned.

[51] Int. Cl.$^4$ ............................................. A61F 5/44
[52] U.S. Cl. ................................................. 604/339
[58] Field of Search ............... 277/124, 181, 185, 125; 285/910, 200; 604/332–345, 256

[56]  References Cited

U.S. PATENT DOCUMENTS

| 2,746,456 | 5/1956 | De Camillis | 604/342 |
| 3,528,420 | 9/1970 | Nielsen | 128/283 |
| 3,557,790 | 1/1971 | Hauser | 604/342 |
| 3,897,781 | 8/1975 | Marson | 604/338 |
| 4,419,100 | 12/1983 | Alexander | 604/339 |
| 4,460,363 | 7/1984 | Steer et al. | 604/336 |
| 4,610,676 | 9/1986 | Schneider et al. | 604/339 |
| 4,610,677 | 9/1986 | Mohiuddin | 604/341 |
| 4,808,173 | 2/1989 | Kay | 604/339 |

Primary Examiner—Jerome L. Kruter
Attorney, Agent, or Firm—Tilton, Fallon, Lungmus

[57] ABSTRACT

An ostomy appliance including a collection pouch, an adhesive faceplate for adherence to a patient, and a coupling ring assembly detachably connecting the pouch and faceplate together. The coupling ring assembly comprises a pair of flexible plastic latching rings capable of being connected together by axially-applied forces and a soft, deformable, sealing ring interposed between, and axially compressed by, opposing wall portions of the latching rings.

10 Claims, 3 Drawing Sheets

U.S. Patent   Dec. 26, 1989   Sheet 1 of 3   4,889,534
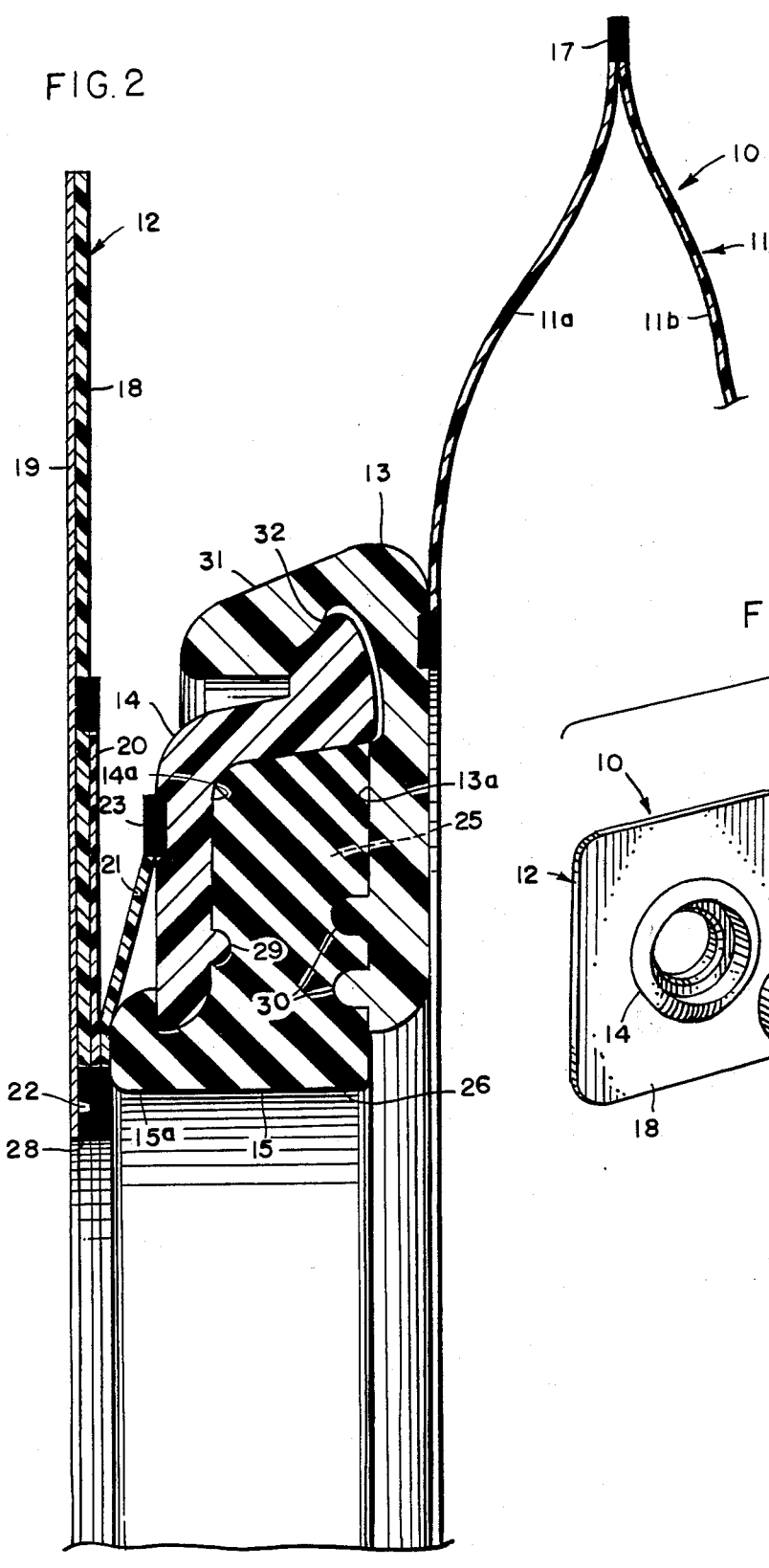
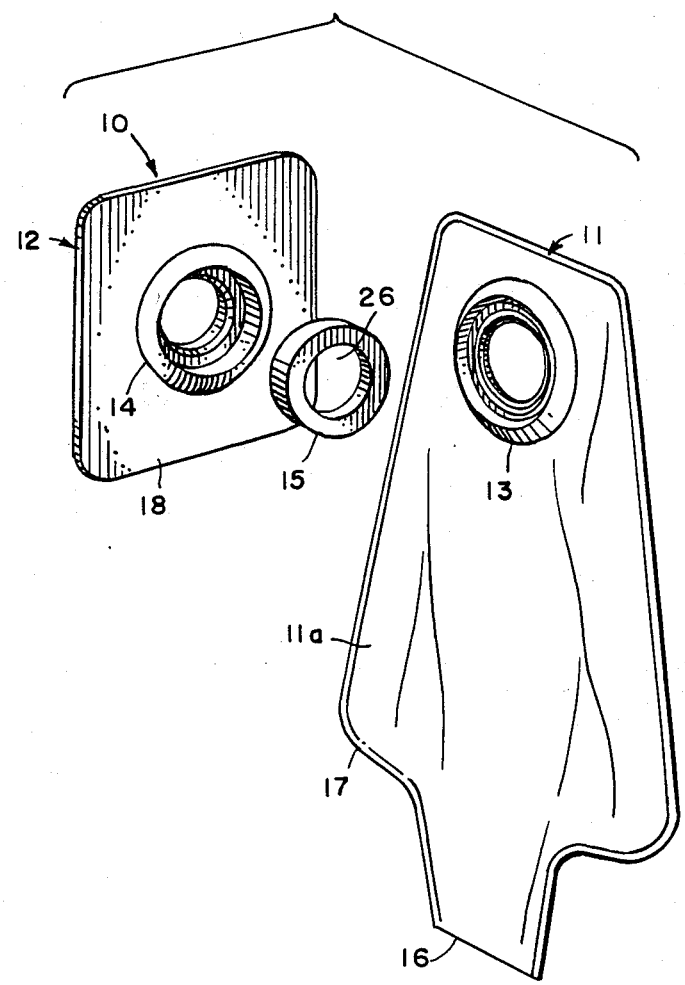

OSTOMY APPLIANCE WITH THREE-LEMENT COUPLING RING ASSEMBLY

BACKGROUND AND SUMMARY

This application is a continuation of application Ser. No. 937,825, filed Dec. 4, 1986, and now abandoned.

Co-owned U.S. Pat. No. 4,610,676 discloses an ostomy appliance with a coupling ring assembly composed of a pair of flat rings of polyethylene or other relatively soft, flexible, plastic material The rings are detachably connected together in an outer latching zone where a radially-deflectable peripheral rim of one of the rings receives the outer edge of the other ring. A fluid-tight seal is formed elsewhere, in an inboard annular sealing zone, where a flexible lip or flange of one of the rings presses radially inwardly against a tubular neck portion of the second ring The idea of forming a fluid-tight seal (i.e., both liquid- and gas-tight) between the coupling rings of an ostomy appliance by means of a radially-deflectable sealing lip or rim that bears inwardly or outwardly against an annular sealing surface is also reflected in other patents such as, for example, U.S. Pats. Nos. 3,528,420, 4,610,677, and 4,460,363.

One aspect of this invention lies in the recognition that while a radially-deflectable rib or rim is well suited for latching a pair of coupling rings together, it is inherently less desirable as the means for performing the function of achieving a fluid-tight seal between the parts. One reason is that such a rib might become scratched, deformed, or otherwise damaged in use with the result that even slight imperfections may result in leakage. Another problem—one which tends to increase production difficulties and expense—is that the thermoplastics from which such coupling rings are formed shrink somewhat unpredictably as they cool to room temperature during manufacture. Shrink factors of over one percent are not uncommon in the injection molding of such plastic materials. Since such rings are relatively flat, shrinkage tends to be far greater in the radial direction than in the axial direction. It is believed apparent that if the element relied upon for achieving a fluid-tight seal in the finished coupling ring assembly is a sealing lip that is radially deflectable and must sealingly engage a radially-facing surface, shrinkage is a variable factor that may present substantial manufacturing problems.

A further aspect of the invention lies in the discovery that such difficulties may be avoided if the latching and sealing mechanisms are separated from each other with the latching function being performed by a radially-deflectable lip or flange (or by other latching means) and with the sealing function being performed by axially-compressible means. Because shrinkage during manufacture in an axial direction is relatively slight, greater uniformity and reliability of the sealing function is thus attainable. Sealing effectiveness is further enhanced by utilizing a soft, compressible sealing ring between the latching rings of the assembly, the sealing ring being axially engaged by both of the latching rings. In preferred embodiments of the invention, the resilient sealing ring is secured to one of the latching rings during manufacture and is axially engaged by one or more annular ribs of the other latching ring. Since the resilient sealing ring is under a state of axial compression when the parts are coupled together, recovery forces exerted in opposite axial directions by the sealing ring tend to urge the latching elements (the outboard annular lip and shoulder of the latching rings) into even tighter latching engagement.

In one of the species disclosed, the deformable sealing ring is a separate element that may be joined by the user to the latching ring of the faceplate and then be forceably engaged by both latching rings as the latching rings are urged axially together. A second species is similar except that the sealing ring is secured during manufacture to one of the latching rings. In both such embodiments, the sealing ring has a smaller inside diameter than both of the latching rings and provides a soft, deformable surface for contact with a patient's stoma. In a third version, the sealing ring is retained within an annular channel of one of the latching rings and is engaged by an annular rib of the other latching ring when the parts are coupled together. In a fourth embodiment, the sealing ring is similarly retained within a channel of one of the latching rings but protrudes from that channel for axial sealing engagement with the other latching ring. In all forms of the invention, the sealing ring may be any of a number of soft, non-permeable, resilient materials. Elastomeric compositions may be used as well as typical skin barrier compositions which are less resilient but have the advantages of providing surface tack. Viscoelastic materials having pressure-sensitive adhesive properties (e.g., a hot-melt adhesive)may be advantageously used. Materials with adhesive properties are desirable not only because they enhance sealing effectiveness but also because they promote a more secure attachment between the parts—that is, the adhesive properties supplement the latching action of the latching rings and require greater force to separate the rings than the force needed to join them.

Other features, objects, and advantages of the invention will become apparent from the specification and drawings.

Drawings

FIG. 1 is a perspective view of ostomy appliance embodying the present invention with the collection pouch and adhesive faceplate, and the coupling rings carried by the respective parts, being shown in separated condition.

FIG. 2 is a greatly enlarged vertical sectional view showing the faceplate, pouch, and coupling ring assembly of FIG. 1.

Detailed Description of Preferred Embodiments

Figure 3:
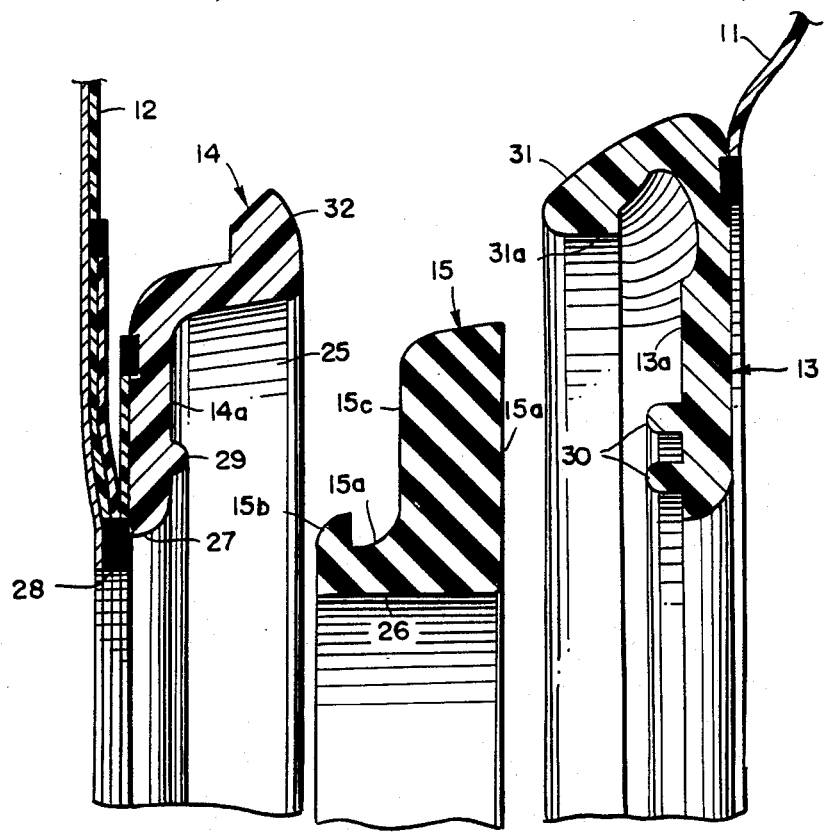
FIG. 3 is a vertical sectional view showing the components of FIG. 2 in separated condition.

FIG. 1 illustrates an ostomy appliance 10 consisting essentially of a collection pouch 11, a faceplate 12, and a coupling ring assembly composed of a first latching ring 13 affixed to the pouch, a second latching ring 14 joined to the faceplate, and a soft, resilient sealing ring 15. Both the pouch and faceplate may vary considerably in size, shape, and construction, all as well known in the art, and it is to be understood that the coupling ring assembly is not limited in its use to the particular pouch and faceplate constructions shown in the drawings. For example, pouch 11 is shown to have an outlet 16 at its lower end, such outlet being intended to be closed by a suitable clamping device (not shown) such as the one disclosed in patent 3,523,534; however, the pouch may if desired be "non-drainable," in which case outlet 16 would be omitted. Typically, pouch 11 is designed to be relatively flat and is composed of two sheets or walls 11a and 11b of flexible thermoplastic film that are heat sealed together along their margins as indicated at 17 in FIG. 2.

Faceplate 12, in the particular form illustrated in the drawings, is constructed generally in accordance with the teachings of U.S. Pat. No. 4,213,458 and reference may be had to that patent for information on the details of construction. Faceplate 12 includes a highly flexible patch or panel 18 of gas-penetrable but water-resistant microporous material. Various materials having such properties are known and may be used. The faceplate should be highly flexible so that it will conform readily to body contours and body movements, and be coated on its back or rear side with a medical-grade pressure-sensitive adhesive so that upon removal of backing sheet or sheets 19 the microporous adhesive-coated patch or panel 18 may be secured to the patient's skin in the peristomal region.

An attaching ring or collar 20 may be secured to the front face of the microporous patch 18 by heat sealing or by any other suitable means. The attaching ring must also be capable of being heat sealed or otherwise securely joined, either directly or indirectly, to the faceplate (second) latching ring 14. In the construction depicted in the drawings, such connection is indirect to the extent that a web 21 of thin, flexible, and resilient thermoplastic material is interposed between faceplate latching ring 14 and the attaching ring 20 of faceplate 12, as generally disclosed in co-owned U.S. Pat. No. 4,419,100. Specifically, the inner margin of the annular web 21 is heat sealed at 22 to the faceplate 12 and its outer margin is heat sealed at 23 to faceplate latching ring 14. The web gives rise to a floating relationship between the latching ring 14 and the faceplate 12, promoting conformity of the faceplate to a wearer's body without resistance from the latching rings and, in general, allowing limited movement of the coupling assembly in generally axial directions with respect to the faceplate. Such limited movement allows a user to insert his (her) fingers between the coupling ring assembly and faceplate 12 to facilitate attachment and detachment of the latching rings without causing discomfort. The web 21 should be formed of a heat-sealable, tough, and durable material that is also capable of functioning as a fluid and odor barrier. Low density polyethylene coextruded with a coextensive layer or core of polyvinylidene chloride, known under the designation Saranex, from Dow Chemical Company, Midland, Michigan, has been found suitable but other materials having similar properties are available and may be used.

The coupling ring assembly, and particularly the structural relationship between pouch latching ring 13, sealing ring 15, and faceplate latching ring 14, are illustrated most clearly in FIGS. 2 and 3. The two latching rings have opposing wall portions 13a and 14a that are generally flat, lie along planes normal to the axis of the coupling ring assembly, and define an annular space or chamber 25 between them when the latching rings are coupled together as shown in FIG. 2. The soft, deformable sealing ring 15 is disposed in that chamber in sealing contact with both of the opposing wall portions 13a, 14a. The opening 26 of sealing ring 15 is aligned with opening 27 of the faceplate latching ring 14 and with the aperture 28 in faceplate 12 (FIG. 3). An axially-extending neck portion 15a of the sealing ring extends through opening 27 of latching ring 14 and an annular enlargement 15b at the end of the neck portion serves the dual purposes of holding the rings 14 and 15 together and urging the web 21 towards faceplate 12 (FIG. 2). Since web 21 normally assumes a planar state, such deflection results in forceful contact between the web and sealing ring and produces an effective seal between those elements.

In the embodiment illustrated in FIGS. 1–3, the sealing ring 15 is not adhered or permanently secured to either of the latching rings 13, 14, although it is apparent that a mechanical interconnection exists between rings 14 and 15 because of the protrusion of neck portion 15a through opening 27 and the terminal enlargement 15b of that neck portion. To insure a fluid-tight seal between wall portion 14a of latching ring 14 and the planar surface 15c of the sealing ring 15, one or more annular ribs 29 may be integrally formed along the surface of wall portion 14a facing the sealing ring. Similarly, the surface of wall portion 13a of pouch latching ring 13 that faces the planar surface 15b of the sealing ring may also be provided with one or more annular ribs 30. Such ribs press into the resilient sealing ring 15 when the parts are assembled as shown in FIG. 2, displacing some of the material of the deformable sealing ring, and creating sealing areas of relatively high force conconcentration to insure a fluid-tight seal between the parts. It will be observed that such forces are exerted upon the sealing ring in generally axial directions; that is, the opposing walls 13a and 14a of the latching rings, and particularly the annular ribs 29, 30 of those walls, place the sealing ring in a state of axial compression.

The latching means for securing the parts together takes the form of a radially-deflectable annular lip 31 of one of the rings (13) which fits over and about an annular peripheral shoulder 32 of the other ring (14). FIG. 3 shows the components of the coupling ring assembly in detached condition, and it will be apparent when rings 13 and 14 are urged towards each other the peripheral lip 31 must stretch or expand radially outwardly to accommodate shoulder 32. When the latching rings are fully connected, the enlarged end or rim 31a of the lip engages the annular shoulder 32 and prevents separation of the latching rings unless forces of sufficient magnitude are exerted to cause the lip 31 to stretch or bend outwardly and release the shoulder. Since the sealing ring 15 is in a state of axial compression when the parts are assembled, any restorative forces exerted by the sealing ring tend to urge the latching rings 13, 14 in opposite axial directions and into even tighter latching engagement with each other. It should be noted, however, that while a secure mechanical latch is thereby achieved between rings 13 and 14, the sealing action responsible for preventing the escape of fluids (liquid and gas) is achieved inboard of the latching zone by tight and forceful axial contact between the deformable sealing ring 15 and the opposing wall portions 13a and 14a of the latching rings.

Figure 4:
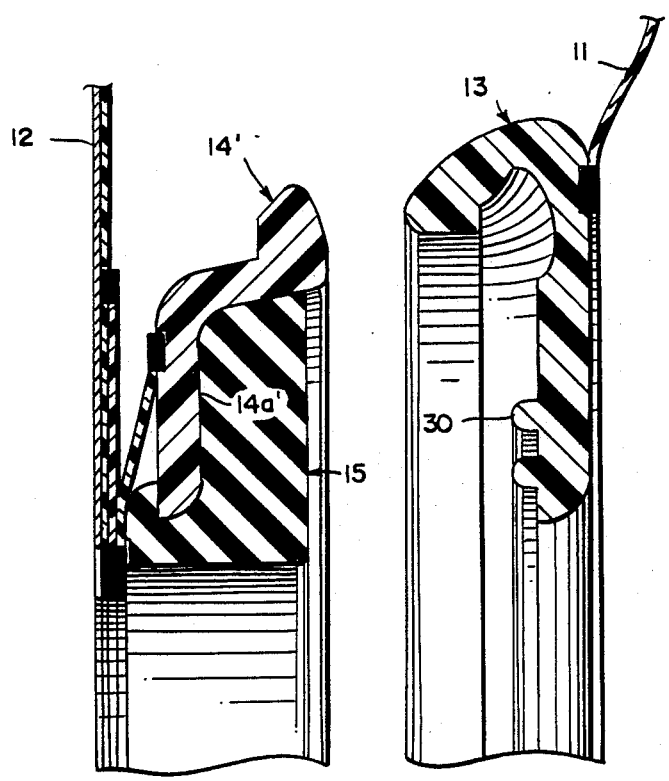
FIG. 4 is a vertical sectional view of a modified construction similar to the embodiment o FIGS. 1-3 but having the sealing ring secured to one of the latching rings.

FIG. 4 illustrates a construction wich is identical to the embodiment of FIGS. 1–3 except that the annular rib 29 is omitted from faceplate latching ring 14' and the sealing ring 15 is secured during manufacture to wall 14a' of the latching ring. Ordinarily such attachment would be an adhesive one resulting either from the provision of an adhesive layer between the opposing surfaces or from adhesive properties of the sealing ring composition. If an adhesive layer is used, it may be of a medical-grade acrylic latex composition or any other suitable pressure-sensitive adhesive composition. Alternatively, other means for permanently sealing rings 14' and 15 together may be employed (such as, for example, heat sealing) depending on the compositions of the elements.

The sealing ring 15 may be composed of any soft, deformable, resilient, non-permeable material. Low durometer elastomers such as silicone rubber, polyurethane, or polybutylene/polyisoprene may be used. Resilient closed-cell foams of polyurethane, polyethylene, or other polymeric materials may also be used. Particularly effective results may be achieved where the sealing ring, in addition to being deformable and elastically recoverable, also has pressure-sensitive adhesive characteristics. Hot melt adhesives having such properties are known and any of a number of them may be used for this purpose. For example, one such material is available under the designation HM6515 from H. B. Fuller Company, St. Paul, Minn. Others are designated as 34-2881 from National Starch & Chemical Corporation, Bridgewater, N.J., and 84116 from Swift Adhesives Division, Reichold Chemicals, Inc., Chicago, Ill. Other deformable sealant materials having adhesive properties are the skin barrier materials widely used in ostomy appliances. Karaya-glycerin formulations, mixtures of polyacrylamide resin and other polyols, and mixtures of elastomers and hydrocolloids may be used. Reference may be had to U.S. Pats. Nos. 4,477,325 and 4,496,357 for a discussion of prior skin barrier compositions and a disclosure of additional compositions having particular advantages which may be utilized here.

The latching rings 13 and 14 are preferably formed of low-density polyethylene, but any other suitable thermoplastic material having similar properties of flexibility and toughness may be used.

Figure 5:
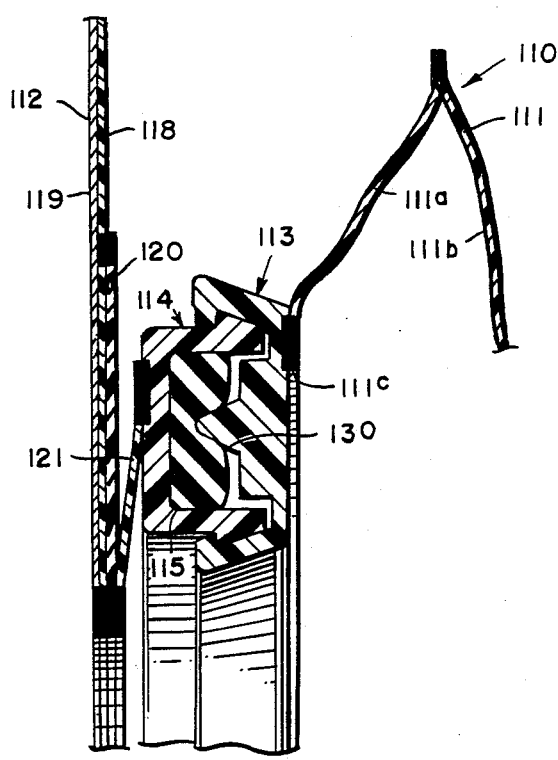
FIG. 5 is a further embodiment shown in assembled condition in fragmentary vertical section.
Figure 6:
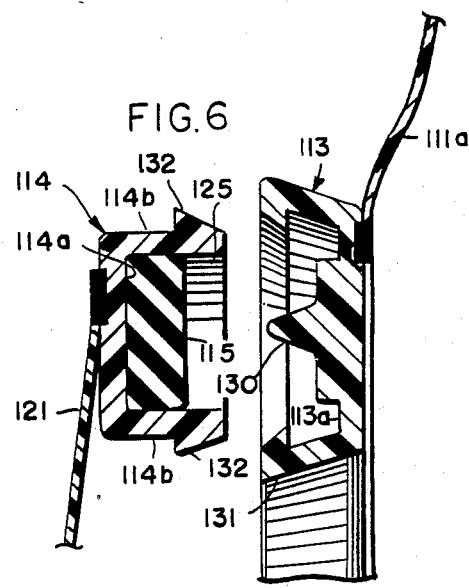
FIG. 6 is a vertical sectional view similar to FIG. 5 but showing the components in detached condition.

FIGS. 5 and 6 illustrate a further embodiment having a faceplate 112 and pouch 111 that may be the same as already described. Thus, faceplate 112 includes a microporous patch 118 with its pressure-sensitive adhesive surface covered by release sheet 119, the patch being connected to the faceplate latching ring by means of an attaching ring or collar 120 and a web 121. The pouch has walls 111a and 111b of thermoplastic film with the proximal wall 111a (the wall facing the patient) being provided with a stomareceiving opening 111c. A first latching ring 113 is secured to the pouch wall 111a about the stoma opening, and a second latching ring 114 is connected to the web 121 of faceplate 112. Interposed between the two latching rings is a soft, deformable sealing ring 115. The three rings together constitute the coupling ring assembly of ostomy appliance 110.

As in the preceding embodiments, latching rings 113 and 114 have opposing wall portions 113a and 114a that together define a chamber 125 when the rings are latched together. The sealing ring 115 is totally confined within that chamber. Wall portion 113a of the pouch coupling ring 113 includes at least one annular rib 130 that is pressed into the normally planar surface of the sealing ring when the parts are coupled together (compare FIGS. 5 and 6). The action is the same as previously described; specifically, the sealing ring 115 is compressed axially between the two latching rings when those latching rings are urged together into the fully-coupled condition shown in FIG. 5.

The faceplate latching ring 114 includes not only the wall portion 114a but also a pair of concentric side wall extensions 114b, each having an annular shoulder 132 facing away from the channel 114c in which the sealing ring 115 is received (FIG. 6). Those shoulders are engaged by the radially-deflectable flanges or lips 131 of the pouch latching ring 113 when the rings are latched together.

The materials of the latching rings 113, 114 and sealing ring 115 may be the same as described in connection with prior embodiments. Sealing ring 115 might be supplied as a separate element to be fitted into chamber 125 by a user but, preferably, the sealing ring is placed or formed within the channel of latching ring 114 during manufacture. It will be noted that the sealing ring does not protrude beyond the channel and, therefore, may be easily made by flowing molten or liquid sealant material into the channel and then allowing it to cure or partially harden into the condition depicted in FIG. 6.

Figure 7:
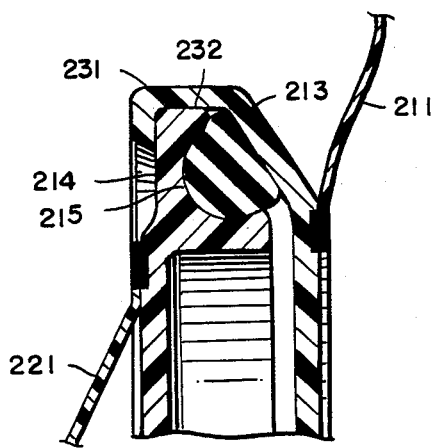
FIG. 7 is a further embodiment showing the parts in fragmentary vertical section and in assembled condition.
Figure 8:
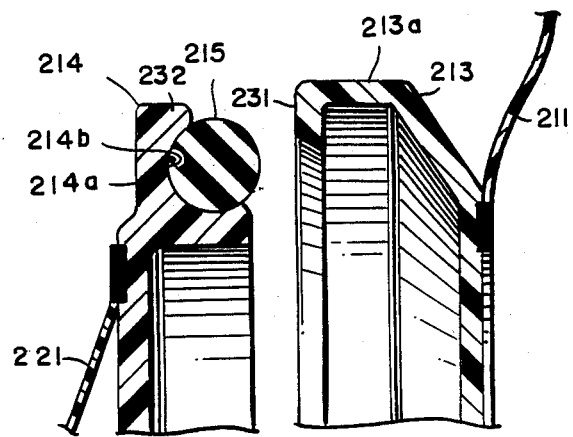
FIG. 8 is a fragmentary vertical sectional view showing the elements of FIG. 7 in disassembled condition.

FIGS. 7 and 8 illustrate an additional embodiment which is identical to earlier forms except for the construction of the coupling ring assembly. Sealing ring 215 is torous-shaped and of circular cross section in an undeformed state (FIG. 8). It is received within the channel 214b of faceplate latching ring 214. The faceplate latching ring 214 and pouch latching ring 213 have opposing wall portions 214a and 213a which place the sealing ring 215 in a state of axial compression when the latching rings are coupled together. Again, the faceplate latching ring 214 includes an annular shoulder 232 engaged by the radially-deflectable lip or flange 231 of the other latching ring when the rings are latched together. The materials of the rings 213–215 may be the same as those described in connection with the other embodiments. While sealing ring 215 may be supplied as a separate component to be fitted into channel 214b at the time of use, the sealing ring 215 and latching ring 214 are preferably supplied to the user in the preassembled condition depicted in FIG. 8.

In all of the embodiments described, the latching rings with the outer radially-deflectable lips or flanges 31, 131, 231 are mounted on the pouches 11, 111, 211, whereas the latching rings with the outwardly-facing shoulders 32, 132, 232 are affixed to the faceplates or to their connecting webs 21, 121, 221. While such an arrangement is preferred, it is to be understood that the respective positions of the latching rings might, if desired, be reversed and that the reversed arrangement would still provide most if not all of the benefits and advantages of this invention.

In the foregoing we have disclosed embodiments of the invention in considerable detail for purposes of illustration, but it will be understood by those skilled in the art that many of these details may be varied without departing from the spirit and scope of the invention.

We claim:

1. An ostomy appliance comprising a collection pouch having a stoma opening therein; an adhesive faceplate having an aperture alignable with said stoma opening; and coupling means for detachably connecting said pouch and faceplate together; said means comprising a first latching ring secured to said pouch about said stoma opening; a second latching ring connected to said faceplate about said aperture; said latching rings being formed of flexible plastic material with one of said rings having an annular shoulder and the other of said rings having a radially-deflectable lip for radially-directed latching engagement with said shoulder when said rings are urged axially together; said lip including a radially-inwardly projecting latching rim; said rim extending behind said shoulder when said latching rings are coupled together to prevent axial separation of said latching rings in the absence of radially-outward deflection of said lip; said latching rings also having axially-aligned openings therethrough and having opposing wall portions extending along planes generally normal to the axes of said aligned openings; said opposing wall portions being spaced axially apart to define an annular chamber therebetween when said latching rings are coupled together; and a sealing ring of soft, deformable, resilient material disposed within said annular chamber in sealing engagement with both of said opposing wall portions, and in a state of axial compression, when said latching rings are coupled together; said opposing wall portions being provided with at least one annular rib projecting axially into said chamber for sealingly engaging and deforming said sealing ring.

2. The appliance of claim 1 in which said sealing ring is secured to said wall portion of one of said latching rings.

3. The appliance of claim 2 in which said sealing ring is secured to said wall portion of said second latching ring.

4. The appliance of claim 3 in which said annular rib is provided by said wall portion of said first latching ring.

5. The appliance of claims 1, 2, 3, or 4 in which said sealing ring is formed of a material having pressure-sensitive adhesive properties.

6. An ostomy appliance comprising a collection pouch having a stoma opening therein; an adhesive faceplate having an aperture alignable with said stoma opening; and coupling means for detachably connecting said pouch and faceplate together; said means comprising a first latching ring secured to said pouch about said stoma opening; a second latching ring connected to said faceplate about said aperture; said latching rings being formed of flexible plastic material with one of said rings having an annular shoulder and the other of said rings having a radially-deflectable lip for latching engagement with said shoulder when said rings are urged axially together; said latching rings also having opposing wall portions spaced apart to define an annular chamber when said latching rings are coupled together; and a sealing ring of soft, deformable, resilient material disposed within said annular chamber in sealing engagement with both of said opposing wall portions, and in a state of axial compression, when said latching rings are coupled together; said sealing ring having an inside diameter smaller than the inside diameters of said latching rings; said sealing ring also being secured to said second latching ring and including a tubular neck portion projecting through the opening of said second latching ring.

7. An ostomy appliance comprising a collection pouch having a stoma opening therein; an adhesive faceplate having an aperture alignable with said stoma opening; and coupling means for detachably connecting said pouch and faceplate together; said means comprising a first latching ring secured to said pouch about said stoma opening; a second latching ring connected to said faceplate about said aperture; said latching rings being formed of flexible plastic material with one of said rings having an annular shoulder and the other of said rings having a radially-deflectable lip for latching engagement with said shoulder when said rings are urged axially together; said latching rings also having opposing wall portions spaced apart to define an annular chamber when said latching rings are coupled together; and a sealing ring of soft, deformable, resilient material disposed within said annular chamber in sealing engagement with both of said opposing wall portions, and in a state of axial compression, when said latching rings are coupled together; said radially-deflectable lip being annular and including a radially-inwardly projecting latching rim; said rim extending behind said shoulder when said latching rings are coupled together to prevent axial separation of said latching rings in the absence of radially outward deflection of said lip; said sealing ring having an inside diameter smaller than the inside diameters of said latching rings; said sealing ring also being secured to said second latching ring and including a tubular neck portion projecting through the opening of said second latching ring.

8. An ostomy appliance comprising a collection pouch having a stoma opening therein; an adhesive faceplate having an aperture alignable with said stoma opening; and coupling means for detachably connecting said pouch and faceplate together; said means comprising a first latching ring secured to said pouch about said stoma opening; a second latching ring connected to said faceplate about said aperture; said latching rings being formed of flexible plastic material with one of said rings having an annular shoulder and the other of said rings having a radially-deflectable lip for latching engagement with said shoulder when said rings are urged axially together; said latching rings also having opposing wall portions spaced apart to define an annular chamber when said latching rings are coupled together; and a sealing ring of soft, deformable, resilient material disposed within said annular chamber in sealing engagement with both of said opposing wall portions, and in a state of axial compression, when said latching rings are coupled together; one of said latching rings being provided with an annular axially-facing channel defined by one of said opposing walls and a pair of spaced concentric side walls formed integrally therewith; said one latching ring including a pair of said latching shoulders provided by said concentric side walls; said other latching ring having a pair of said deflectable lips engagable with said shoulders for latching engagement with said shoulders when said rings are urged together; said sealing ring being disposed within said channel.

9. An ostomy appliance comprising a collection pouch having a stoma opening therein; an adhesive faceplate having an aperture alignable with said stoma opening; and coupling means for detachably connecting said pouch and faceplate together; said means comprising a first latching ring secured to said pouch about said stoma opening; a second latching ring connected to said faceplate about said aperture; said latching rings being formed of flexible plastic material with one of said rings having an annular shoulder and the other of said rings having a radially-deflectable lip for latching engagement with said shoulder when said rings are urged axially together; said latching rings also having opposing wall portions spaced apart to define an annular chamber when said latching rings are coupled together; and a sealing ring of soft, deformable, resilient material disposed within said annular chamber in sealing engagement with both of said opposing wall portions, and in a state of axial compression, when said latching rings are coupled together; said one of said latching rings being provided with an annular axially-facing channel defined by one of said opposing walls and a pair of spaced concentric side walls formed integrally therewith; said one latching ring having said channel being said latching ring and including a pair of said latching shoulders provided by said concentric side walls; said other latching ring having a pair of said deflectable lips engagable with said shoulders for latching engagement with said shoulders when said rings are urged together; said sealing ring being disposed within said channel.

10. The appliance of claim 8 or 9 in which said shoulders are disposed along the external surfaces of said side walls opposite from said channel.

* * * * *